United States Patent [19]
Straub

[11] Patent Number: 5,876,414
[45] Date of Patent: Mar. 2, 1999

[54] CATHETER FOR DETACHING ABNORMAL DEPOSITS FROM BLOOD VESSELS IN HUMANS

[75] Inventor: Immanuel Straub, Wangs, Switzerland

[73] Assignee: Straub Medical AG, Wangs, Switzerland

[21] Appl. No.: 913,951

[22] PCT Filed: Mar. 7, 1996

[86] PCT No.: PCT/CH96/00086

§ 371 Date: Sep. 29, 1997

§ 102(e) Date: Sep. 29, 1997

[87] PCT Pub. No.: WO96/29942

PCT Pub. Date: Oct. 3, 1996

[30] Foreign Application Priority Data

Mar. 28, 1995 [CH]  Switzerland ............................. 874/95

[51] Int. Cl.⁶ .................................................. A61B 17/22
[52] U.S. Cl. ............................................. 606/159; 604/22
[58] Field of Search ..................... 606/159, 170, 606/180; 604/22

[56] References Cited

U.S. PATENT DOCUMENTS

| | | |
|---|---|---|
| 3,320,957 | 5/1967 | Sokolik . |
| 4,857,046 | 8/1989 | Stevens . |
| 4,955,882 | 9/1990 | Hakky . |
| 5,226,909 | 7/1993 | Evans et al. ............................. 606/159 |
| 5,269,751 | 12/1993 | Kaliman . |
| 5,383,884 | 1/1995 | Summers . |
| 5,571,122 | 11/1996 | Kelly et al. ............................. 606/159 |

FOREIGN PATENT DOCUMENTS

A 0 448 859  10/1991  European Pat. Off. .

OTHER PUBLICATIONS

The Practice of Interventional Cardiology, Chapter 13, Percutaneous Transluminal Coronary Rotary Ablation with the Rotablator, pp. 141–147, Michel E. Bertrand, et al.

The Practice of Interventional Cardiology, Chapter 14, Coronary Atherectomy with the TEC Device, Michael H. Sketch, Jr., et al., pp. 149–155.

The Practice of Interventional Cardiology, Chapter 15, Directional Coronary Atherectomy, Matthew R. Selmon, et al., pp. 157–169.

The Practice of Interventional Cardiology, Chapter 16, Percutaneous Rotational Thrombectomy: An Alternative Approach to Thrombolysis, pp. 171–176, Timothy A. Dewhurst, et al.

*Primary Examiner*—Michael Buiz
*Assistant Examiner*—Kevin Truong
*Attorney, Agent, or Firm*—Oblon, Spivak, McClelland, Maier & Neustadt, P.C.

[57] ABSTRACT

The catheter connected to a rotary drive mechanism has, at its front end, a cutting tool which consists of a stator and rotor. Cutting edges arranged on the circumference of the rotor and stator interact in a shearing action. The detached deposits are conveyed through a tubular sheath and into a collection container via a discharge chamber. A drive shaft which is arranged inside the tubular sheath, and which connects the rotary drive mechanism to the rotor, is designed as a conveyor screw and is used for the conveying. A rotary catheter of this kind is used for carefully removing and withdrawing blood clots and stenoses from narrowed blood.

13 Claims, 2 Drawing Sheets

CATHETER FOR DETACHING ABNORMAL DEPOSITS FROM BLOOD VESSELS IN HUMANS

BACKGROUND OF THE INVENTION

The invention relates to a catheter of the type known as a rotary catheter.

A catheter of this kind is used in particular for treating occlusive diseases of the arteries by dislodging stenoses and breaking up blood clots. It is introduced into the artery and is advanced as far as the stenosed area which is to be treated. A cutting tool which can be driven in rotation is arranged at its front or leading end.

DISCUSSION OF THE BACKGROUND

A known catheter, for example the one from EP-B1-0, 267,539, has as its cutting tool a substantially elliptical milling cutter which is provided with abrasive material on its surface and is driven at a speed of up to 160,000 rpm. The milling cutter is connected via a flexible drive shaft to a rotary drive mechanism which is arranged at the other end of the catheter. The drive shaft runs inside a tubular sheath which serves as a catheter tube. A guide wire extending right through the drive shaft is introduced into the artery before introduction of the catheter and is advanced right through the stenosis.

In this known rotary catheter, the particles which are dislodged by the milling cutter are not removed from the body, since they should normally be smaller than the red blood cells by about 7 m. If, however, some of the particles which have been dislodged are larger than red blood cells, then there is a considerable risk of their blocking the bloodstream at another location and thereby causing an embolism.

From the literature, it is also known for the particles which have been dislodged to be drawn off through the catheter by suction. Here, however, there is the risk that too many particles will fail to be caught and that these will thus pass into the bloodstream.

The invention is therefore based on the object of providing a catheter which is of the type mentioned at the outset and in which the particles which have been dislodged are removed from the circulation almost in their entirety.

According to the invention, these and other objects are accomplished by providing a catheter comprised of a tubular sheath, a cutting tool provided at a front end of the sheath and the flexible drive shaft provided within the sheath which connects the cutting tool with the rotary drive mechanism. The flexible drive shaft is formed with a helical shape such that it conveys dislodged deposits recovered by the cutting tool axially along the length of the tubular sheath. By providing the catheter with a helically shaped drive shaft provided within a tubular sheath, the catheter according to the present invention ensures an immediate and continuous withdrawal of the dislodged or detached particles, so as to reliably prevent these particles from passing into the circulation of the bloodstream.

In one embodiment of the invention, the flexible drive shaft can be constructed of a helically wound wire, which is a particularly convenient form for the drive shaft to be constructed of.

The flexible drive shaft of the above embodiment can optionally be constructed of a helically wound wire that has a substantially rectangular cross section. By using a wire with a substantially rectangular cross section, the resulting helically wound flexible drive shaft with a higher surface area and therefore a higher conveying capacity since the surface area of a square cross section is greater than that of, for example, a round wire cross section.

The flexible drive shaft of the above embodiment can also, optionally, be coated thereby making it possible, on the one hand, to choose freely a material which is particularly suitable as to strength, and, on the other hand, to provide an appropriate protection against corrosion and satisfy corresponding requirements in respective hygiene and tribiology.

According to a further embodiment of the present invention, a cutting tool can be provided with a slot through which detached deposits are passed into the cutting tool, and the flexible drive shaft can be extended into the inside of the cutting tool. By providing the flexible drive shaft as such, the particles or detached deposits pass through the slot and onto the flexible drive shaft, thereby avoiding detached particles passing into the bloodstream.

In a further embodiment, the cutting tool may be provided with a stator which can rotate with respect to the rotor such that cutting edges provided in the rotor and stator cooperate to provide a shearing action. By producing a shearing action, in contrast to the use of freely cutting blades, improved control of the dislodging of the deposits is achieved, and in doing so, the risk of damage to the blood vessel walls is also reduced. In particular, with such an embodiment it is also easier to ensure that the particles which have been dislodged will in all possibility pass through the slot or slots into the region of the conveyor screw and are thus kept from entering the bloodstream.

In yet another further embodiment of the present invention, the stator and rotor are constructed substantially cylindrically such that the stator is provided within the rotor which thereby ensures that the rotor attacks the deposits radially so that it is not possible, for example in the area of curves in an artery, to drill straight into the vessel wall.

BRIEF DESCRIPTION OF THE DRAWINGS

An illustrative embodiment of the invention is explained in greater detail with reference to the drawings, in which.

DISCUSSION OF THE PREFERRED EMBODIMENTS

Figure 1:
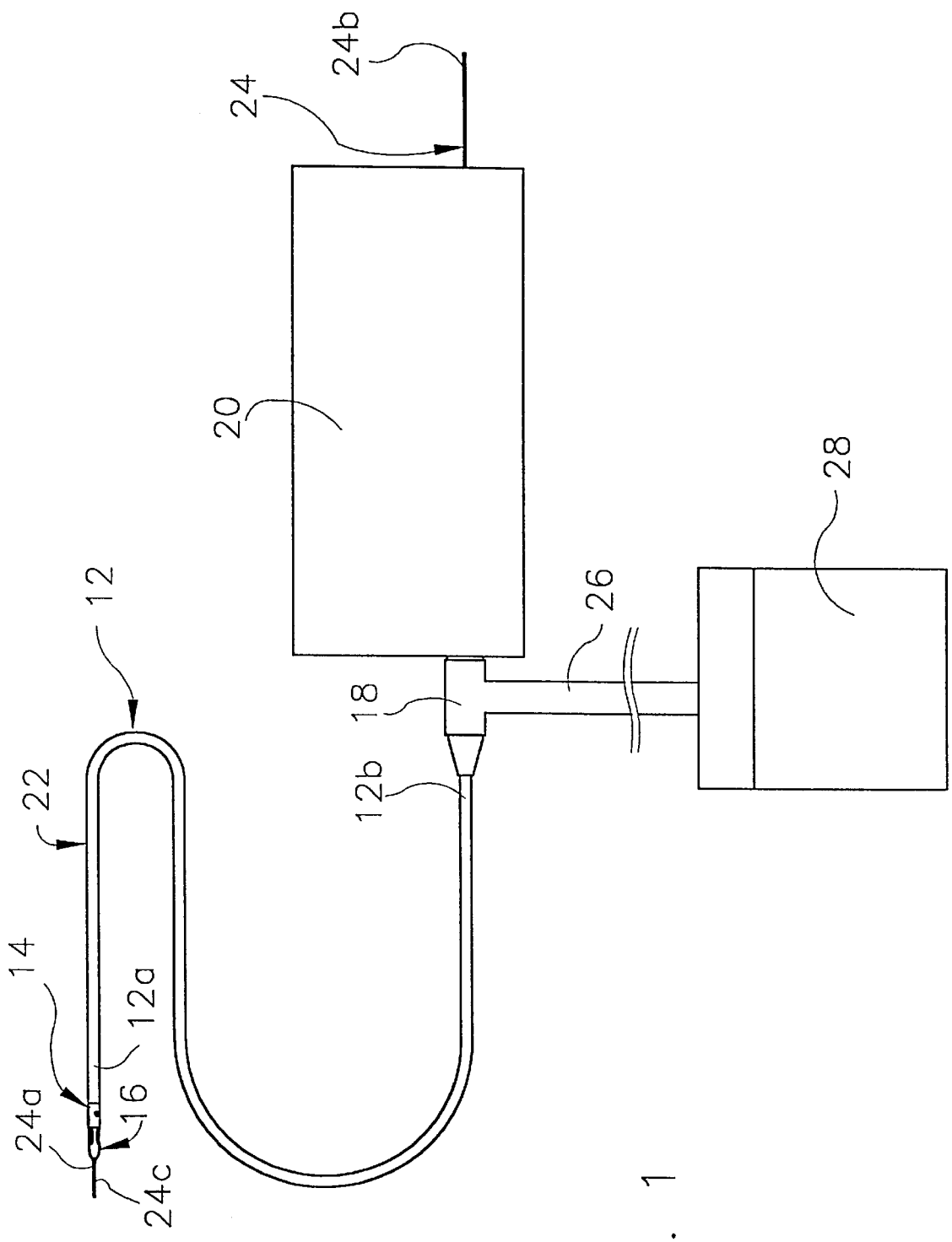
FIG. 1 shows a rotary catheter in a general view, with drive mechanism, guide wire and collection container for the deposit fragments detached from the blood vessel.

The catheter 12 shown in FIG. 1 has, at its front end 12a, a cutting tool which consists of a stator 14 and rotor 16. At its rear end 12b, the catheter 12 is connected to a rotary drive mechanism 20 via a discharge chamber 18. A flexible drive shaft is mounted in a tubular sheath 22 which serves as catheter tube, said drive shaft connecting the rotor 16 to the rotary drive mechanism 20. A guide wire 24 extends right through the entire length of the catheter 12, and its front end 24a protrudes from the rotor 16 and its rear end 24b from the rotary drive mechanism 20. The guide wire 24 has a nib point 24c at its front end 24a. A collection container 28 is linked to the discharge chamber 18 in the radial direction via a tube or a pipe 26.

When using the catheter 12, the guide wire 24 is introduced, with its front end 24a leading, into the artery or vein which is to be treated, and it is then advanced as far as the stenosed area and manoeuvred through the latter, with radiographic monitoring. The catheter 12 is then passed along the guide wire 24. As soon as the front end 12a has reached the area which is to be treated, the rotary drive mechanism 20 is switched on in order to detach the undesired deposits by means of the cutting tool 14, 16 and to convey them out of the bloodstream. The speed of rotation of the rotor 16 preferably lies in the range between 30,000 and 40,000 rpm. The catheter 12 is advanced slowly as the operation proceeds. The deposits which have been dislodged and broken up are carried off through the tubular sheath 22 as far as the discharge chamber 18 and they pass from there into the collection container 28.

Figure 2:
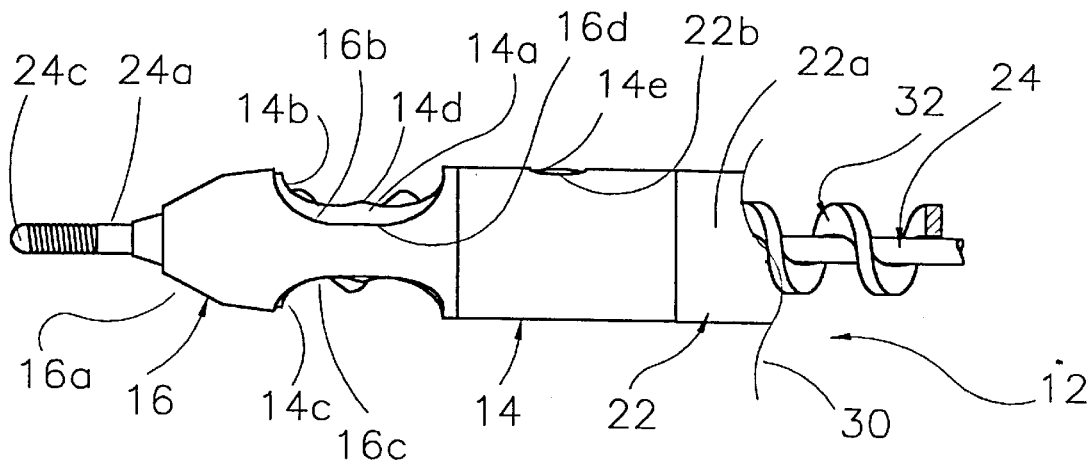
FIG. 2 shows a plan view of the head part of the rotary catheter according to FIG. 1, but on a larger scale.
Figure 3:
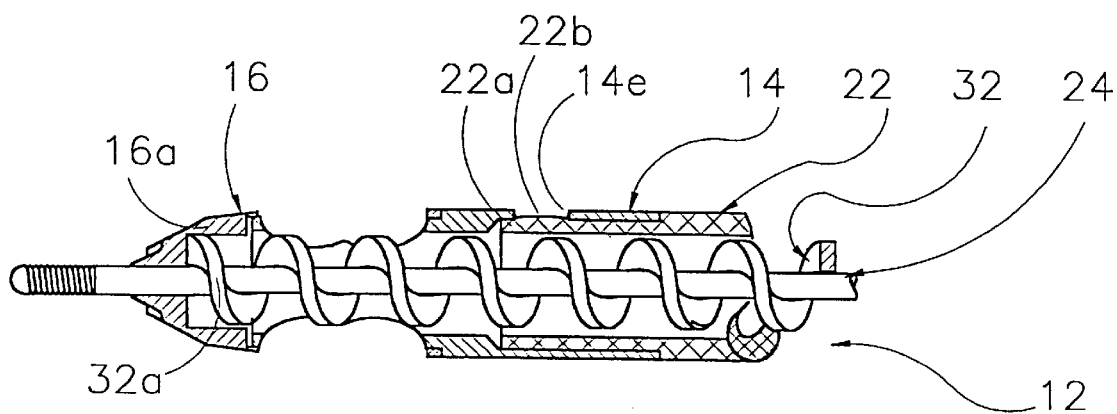
FIG. 3 shows a longitudinal section through the head part of the rotary catheter according to FIG. 2.

FIGS. 2 and 3 show the front end 12a of the catheter 12 with its stator 14, its rotor 16 designed as external rotor, its tubular sheath 22, and the front end 24a of the guide wire 24. The tubular sheath 22 is shown cut away at 30 in order to reveal the flexible drive shaft 32 whose front end 32a is fixed to the rotor 16 in terms of rotation and tensioning. The guide wire 24 runs through the inside of the drive shaft 32. The drive shaft 32 is designed as a conveyor screw in order to convey the deposits, which have been dislodged by the cutting tool 14, 16, through the tubular sheath 22 to the discharge chamber 18 (FIG. 1).

A portion 14a of the stator 14 extends into the rotor 16. It can be seen that the stator portion 14a and the rotor 16 engage one within the other like a bushing. The stator portion 14a has two shearing slots 14b, 14c which are offset 180° to each other about the circumference. The rotor 16 likewise has two shearing slots 16b, 16c which are offset 180° to each other about the circumference.

The slot 14b of the stator portion 14a is narrower than that 16b of the rotor 16 in the circumferential direction. One margin of the rotor slot 16b is designed as cutting edge 16d. The opposite margin of the stator slot 14b is designed as opposite cutting edge 14d. This opposite cutting edge 14d runs, in the axial direction, in an at least approximately undulating configuration relative to a cylindrical surface.

The cutting edge 16d and the opposite cutting edge 14d interact in a shearing action. Cutting edges of this type are in each case arranged offset 180° to one another about the circumference in both slots 14c, 16c which are also referred to as shearing slots.

Towards its tip, the rotor 16 has a front end 16a of diminishing diameter. In this way, the stenosed area of the artery or vein to be treated is widened upon insertion of the catheter 12.

The rotor 16 and stator 14 are preferably made of metal. The guide wire 24 with the nib tip 24c is a steel wire. The drive shaft 32 serving as conveyor screw consists of a coated steel wire, for example. The tubular sheath 22 is made of plastic.

For connecting the stator 14 to the tubular sheath 22 in a rotationally fixed manner, the end 22a of the latter is press-fitted into the stator 14. For securing purposes, holes 14e are arranged in the circumferential surface of the stator 14, and the pressed-in tube material 22b swells with a positive fit into said holes 14e.

FIG. 3 shows in particular that the drive shaft 32 extends into the front end 16a of the rotor 16, and its front end 32a is fixed to the rotor 16 in terms of rotation and tensioning, for example press-fitted into the latter. The figure also shows how the tubular sheath 22 is secured with a positive fit in the stator 14 by means of the holes 14e.

Figure 4:
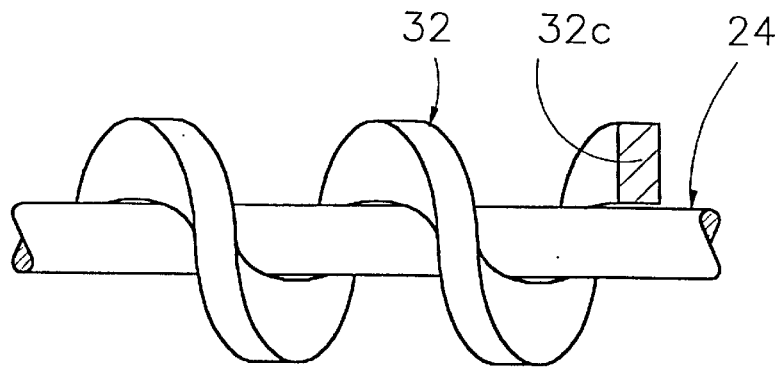
FIG. 4 shows the guide wire and conveyor screw on a still larger scale.

FIG. 4 shows the rectangular cross-section of the wire 32c of the helical drive shaft 32 serving as conveyor screw. The arrangement of the guide wire 24 coaxially inside the drive shaft 32 results in a particularly high degree of efficacy as conveyor screw. The dislodged fragments of the deposits are conveyed in a virtually linear manner inside the catheter tube 22.

I claim:

1. A catheter for detaching abnormal deposits from blood vessels in humans comprising:
    a tubular sheath;
    a cutting tool arranged at a front end of said tubular sheath, said cutting tool including a rotor;
    a rotary drive mechanism;
    a flexible drive shaft provided within said tubular sheath, said flexible drive shaft including a first end configured to connect with said rotor, said flexible drive shaft including a second end configured to connect with said rotary drive mechanism, said flexible drive shaft having a helical shape such that it conveys dislodged deposits axially along said tubular sheath when said flexible drive shaft is rotated by said rotary drive mechanism; and
    a guide wire provided coaxially within said flexible drive shaft such that said guide wire can be moved independently of said flexible drive shaft and said tubular sheath.

2. A catheter according to claim 1, wherein said flexible drive shaft comprises a helically wound wire.

3. A catheter according to claim 2, wherein said cutting tool includes at least one slot configured to convey deposits into said cutting tool and wherein said drive shaft extends into said cutting tool.

4. A catheter according to claim 2, wherein said helically wound wire has a substantially rectangular cross-section.

5. A catheter according to claim 4, wherein said cutting tool includes at least one slot configured to convey deposits into said cutting tool and wherein said drive shaft extends into said cutting tool.

6. A catheter according to claim 4, wherein said helically wound wire is coated.

7. A catheter according to claim 6, wherein said cutting tool includes at least one slot configured to convey deposits into said cutting tool and wherein said drive shaft extends into an inside of said cutting tool.

8. A catheter according to claim 1, wherein said cutting tool includes at least one slot configured to convey deposits into said cutting tool and wherein said drive shaft extends into said cutting tool.

9. A catheter according to claim 8, wherein said cutting tool further comprises a stator provided on said front end of said tubular sheath such that said stator is rotatable relative to said rotor, said stator including at least one stator cutting edge;
    wherein said rotor further comprises at least one rotor cutting edge arranged such that said rotor cutting edge and said stator cutting edge cooperate to produce a shearing action when said rotor is rotated relative to said stator.

10. A catheter according to claim 9, wherein said rotor is substantially cylindrical in a portion including said at least one rotor cutting edge and said stator is substantially cylindrical in a portion including said at least one stator cutting edge, wherein said rotor substantially surrounds said stator, wherein said at least one rotor cutting edge is provided in a circumferential surface of said rotor and wherein said at least one stator cutting edge is provided on a circumferential surface of said stator.

11. A catheter according to claim 10, wherein said at least one slot comprises:

- a stator shearing slot provided on said circumferential surface of said stator wherein said stator cutting edge is provided on an edge of said stator shearing slot; and
- a rotor shearing slot provided on said circumferential surface of said rotor wherein said rotor cutting edge is provided on an edge of said rotor shearing slot.

12. A catheter according to claim 11, wherein at least two stator shearing slots are provided uniformly around said circumferential surface of said stator.

13. A catheter according to claim 11, wherein at least two rotor shearing slots are provided uniformly around said circumferential surface of said rotor.

\* \* \* \* \*